(12) United States Patent
Matsui et al.

(10) Patent No.: US 7,273,704 B2
(45) Date of Patent: Sep. 25, 2007

(54) METHOD OF DETECTING NUCLEIC ACID BY USING DNA MICROARRAYS AND NUCLEIC ACID DETECTION APPARATUS

(75) Inventors: Takuya Matsui, Hitachinaka (JP); Yuji Miyahara, Tsukuba (JP); Kumiko Hattori, Kashiwa (JP)

(73) Assignee: Hitachi High-Technologies Corporation, Tokyo (JP)

( * ) Notice: Subject to any disclaimer, the term of this patent is extended or adjusted under 35 U.S.C. 154(b) by 233 days.

(21) Appl. No.: 10/522,991

(22) PCT Filed: Aug. 12, 2002

(86) PCT No.: PCT/JP02/08212

§ 371 (c)(1),
(2), (4) Date: Feb. 2, 2005

(87) PCT Pub. No.: WO2004/017068

PCT Pub. Date: Feb. 26, 2004

(65) Prior Publication Data

US 2006/0088839 A1    Apr. 27, 2006

(51) Int. Cl.
*C12Q 1/68* (2006.01)
*C07H 21/02* (2006.01)
*C07H 21/04* (2006.01)

(52) U.S. Cl. .................. 435/6; 536/23.1; 536/24.3
(58) Field of Classification Search ............ 435/6; 536/23.1, 24.3
See application file for complete search history.

(56) References Cited

U.S. PATENT DOCUMENTS 6,203,981 B1   3/2001   Ackley et al.
7,011,947 B2 *  3/2006   Golub et al. .............. 435/6
2001/0018185 A1   8/2001   Akimoto
2001/0034030 A1  10/2001   Hefti
2002/0098496 A1   7/2002   Lipshutz et al.
2004/0161801 A1 * 8/2004   Ban et al. .............. 435/7.1
2005/0064426 A1 * 3/2005   Zou et al. ............... 435/6

FOREIGN PATENT DOCUMENTS

| EP | 1010764 | 6/2000 |
| EP | 1158449 | 1/2002 |
| JP | 2001-299346 | 10/2001 |
| JP | 2001-321198 | 11/2001 |

OTHER PUBLICATIONS

Lockhart et al. Expression Monitoring by hybridization to high-density oligonucleotide arrays. Nature Biotechnology 14 : 1675-1680 (Dec. 1996).*

* cited by examiner

*Primary Examiner*—Ethan Whisenant
(74) *Attorney, Agent, or Firm*—Dickstein Shapiro LLP (57) ABSTRACT

A nucleic acid contained in a sample is quantified with high accuracy. The procedure includes the step of allowing the sample containing a specific nucleic acid to interact with a DNA microarray provided with a plurality of nucleic acid probe parts having a nucleic acid probe capable of hybridizing to the specific nucleic acid; the step of monitoring outputs from each of the plurality of nucleic acid probe parts due to hybridization between the nucleic acid probe and the specific nucleic acid to determine normal distribution of time taken to reach a predetermined output value with respect to each of the plurality of nucleic acid probe parts; and the step of quantifying the specific nucleic acid contained in the sample based on a maximum value determined from the normal distribution obtained in the above step.

4 Claims, 9 Drawing Sheets

METHOD OF DETECTING NUCLEIC ACID BY USING DNA MICROARRAYS AND NUCLEIC ACID DETECTION APPARATUS

TECHNICAL FIELD

The present invention relates to a method of detecting nucleic acid by using DNA microarrays, a nucleic acid detection apparatus, and the DNA microarrays that are used in the field of biotechnology such as genetic diagnosis, sequence analysis of DNA, or analysis of gene polymorphism, and particularly in the field of genetic testing.

BACKGROUND ART

Rapid progress has been made in the projects of genome sequence analysis for various living organisms including the human genome project, and enormous amounts of information on the nucleotide sequences are being accumulated. At present, the entire nucleotide sequence of the human genome is being determined. From now on, elucidation of gene functions in vivo seems likely to promote dramatic developments of gene-related technologies in a wide range of fields including diagnosis of various diseases, pharmaceutical development, breeding of agricultural products, and the like. The foundation for the progress in these new fields is formed by information about gene expression and gene function in addition to information on nucleotide sequences. As a technology to perform the analysis of gene function and gene expression in a large scale and to develop it to genetic testing, DNA chip or DNA microarray (hereinafter, collectively called DNA microarray) has been developed by Affymetrix Inc., Nanogen Inc., and so on. The majority of the present DNA microarrays utilizes detection by fluorescence as a basic technique and requires a laser or complex optical system. Therefore, the system becomes large in size and expensive.

Furthermore, DNA microarrays developed currently detect the presence or absence of genes in a sample. On the other hand, there are few DNA microarrays that allow genes in a sample to be quantified.

Hence, in light of the abovementioned circumstances, the object of the present invention is to provide a method of detecting nucleic acid by using DNA microarrays, a nucleic acid detection apparatus, and the DNA microarrays that allow a nucleic acid contained in a sample to be quantified with high accuracy.

DISCLOSURE OF THE INVENTION

The present invention in which the above object was achieved includes the following:

1) A method of detecting nucleic acid by using DNA microarrays comprises the steps of allowing a sample containing nucleic acids to interact with a DNA microarray comprising a plurality of nucleic acid probe parts having a nucleic acid probe capable of hybridizing to a specific nucleic acid; monitoring outputs from each of the plurality of nucleic acid probe parts due to hybridization between the nucleic acid probe and the specific nucleic acid to determine frequency distribution of times when the outputs exceed a predetermined value with respect to each of the plurality of nucleic acid probe parts; and quantifying the specific nucleic acid contained in the sample based on an average value determined from the frequency distribution obtained in the above step.

2) The method of detecting nucleic acid by using DNA microarrays according to claim 1, in which the DNA microarray is formed by immobilizing the nucleic acid probe on the surface of gate insulator directly or via a carrier and comprises a plurality of insulated gate field effect transistors corresponding to the plurality of nucleic acid probe parts; and outputs from the insulated gate field effect transistors are monitored.

3) The method of detecting nucleic acid by using DNA microarrays according to according to claim 1, in which, in the step of allowing the sample containing nucleic acids to interact with the DNA microarray, nucleic acid amplification is carried out on the DNA microarray using the nucleic acid as a template.

4) The method of detecting nucleic acid by using DNA microarrays according to according to claim 3, in which the nucleic acid amplification is carried out by an isothermal amplification method.

5) A nucleic acid detection apparatus comprises a measuring unit to attach a DNA microarray comprising a plurality of nucleic acid probe parts having a nucleic acid probe capable of hybridizing to a specific nucleic acid; detecting units that detect outputs from each of the nucleic acid probe parts of the DNA microarray attached on the measuring unit; and a computing unit that determines frequency distribution of times when the outputs detected by the detecting units exceed a predetermined value with respect to each of the plurality of nucleic acid probe parts and quantifies the specific nucleic acid contained in a sample based on an average value determined from the frequency distribution.

6) The nucleic acid detection apparatus according to claim 5, in which the DNA microarray is formed by immobilizing the nucleic acid probe on the surface of gate insulator directly or via a carrier and comprises a plurality of insulated gate field effect transistors corresponding to the plurality of nucleic acid probe parts; and the detecting units monitor outputs from the insulated gate field effect transistors.

7) The nucleic acid detection apparatus according to claim 5, in which the DNA microarray comprises a plurality of sections having the plurality of nucleic acid probe parts; and time taken for hybridization between the specific nucleic acid and the nucleic acid probe is different in each section.

8) A DNA microarray comprises a plurality of nucleic acid probe parts comprising a nucleic acid probe capable of hybridizing to a specific nucleic acid.

9) The DNA microarray according to claim 8, comprising detecting units that are arranged so as to correspond to the plurality of nucleic acid probe parts and detect hybridization between the specific nucleic acid and the nucleic acid probe.

10) The DNA microarray according to claim 9, in which the detecting units are insulated gate field effect transistors.

11) The DNA microarray according to claim 8, comprising a plurality of sections having the plurality of nucleic acid probe parts, wherein time required for hybridization between the specific nucleic acid and the nucleic acid probe is different in each of the plurality of sections.

12) The DNA microarray according to claim 8, comprising the plurality of sections having the plurality of nucleic acid probe parts, wherein a density of the nucleic acid probe in the nucleic acid probe part differs in each of the plurality of sections.

13) The DNA microarray according to claim 8, comprising the plurality of sections having the plurality of nucleic acid probe parts, wherein an area of the nucleic acid probe part differs in each of the plurality of sections.

14) The DNA microarray according to claim 8, comprising the plurality of sections having the plurality of nucleic acid probe parts, wherein a length of the nucleic acid probe differs in each of the plurality of sections.

BEST MODE FOR CARRYING OUT THE INVENTION

The present invention is explained in detail with reference to the accompanying drawings. In the following drawings, the same functional elements are explained by designating the same reference numerals.

FIRST EMBODIMENT

In a first embodiment, a method of detecting a single nucleotide polymorphism contained in a specified gene (hereinafter, referred to as target gene) is explained in application of the method of detecting nucleic acid according to the present invention.

Figure 1:
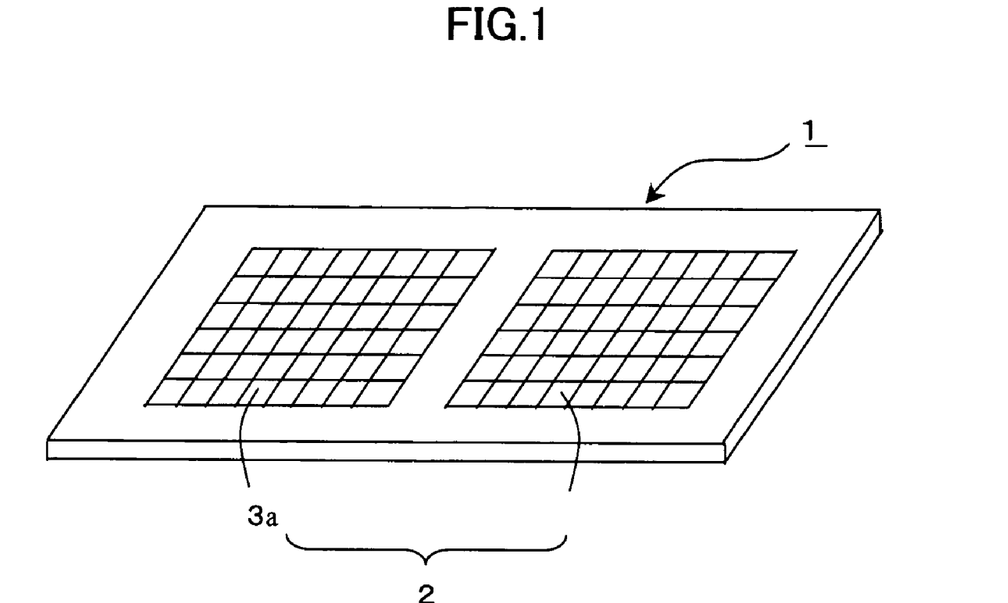
FIG. 1 is a schematic perspective view of a DNA microarray to which the present invention is applied.
Figure 2:
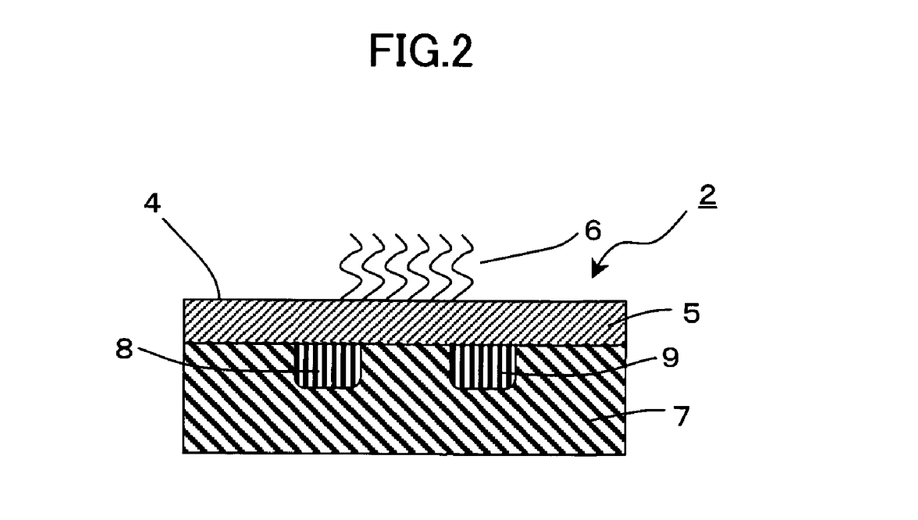
FIG. 2 is a cross sectional view of an essential part of the DNA microarray.

FIG. 1 represents a schematic perspective view of a DNA microarray 1 used in the present method, and FIG. 2 represents a cross sectional view of an essential part of the DNA microarray 1. The DNA microarray 1 comprises, as shown in FIG. 1, a plurality of nucleic acid probe parts 2 arranged on a matrix and insulated gate field effect transistors 3 arranged so as to correspond to the plural probe parts 2. In the DNA microarray 1 of the present embodiment, the plural nucleic acid probe parts 2 are divided into two (called a first region 3a and a second region 3b, respectively). In the first region 3a, one polymorphism (hereinafter, sometimes called "first polymorphism") of the target gene is detected, and in the second region 3b, the other polymorphism (hereinafter, sometimes called "second polymorphism") of the target gene is detected.

The nucleic acid probe part 2 has a structure in which a nucleic acid probe 6 is immobilized on the surface of a gate insulator 5 of the insulated gate field effect transistor 4. The insulated gate field effect transistor 4 is provided with, for example, a source 8 that serves as supply source of carrier and is arranged on a p-type silicon substrate 7, a drain 9 that takes out the carrier, and the gate insulator 5 that is placed on the p-type silicon substrate 7, the source 8, and the drain 9.

The nucleic acid probe 6 is an oligonucleotide, c-DNA, or branched DNA fragment that can hybridize to the target gene to be detected. It is desirable that the nucleic acid probe 6 is generally composed of 300 or less nucleotides, is able to hybridize to the target gene to be detected under an appropriate reaction condition, and in the case of oligonucleotide, is a nucleic acid fragment with a length of 80 or less nucleotides.

In the DNA microarray 1 of the present embodiment, the nucleic acid probe 6 in the first region 3a has a sequence capable of hybridizing to the target gene of the first polymorphism and incapable of hybridizing to the target gene of the second polymorphism. On the other hand, the nucleic acid probe 6 in the second region 3b has a sequence capable of hybridizing to the target gene of the second polymorphism and incapable of hybridizing to the target gene of the first polymorphism.

For the gate insulator 5, it is preferred that a material such as silicon dioxide ($SiO_2$), silicon nitride (SiN), aluminum oxide ($Al_2O_3$), or tantalum oxide ($Ta_2O_5$) is used alone or in combination, and that a bilayer structure in which silicon nitride (SiN), aluminum oxide ($Al_2O_3$), and tantalum oxide ($Ta_2O_5$) are layered on top of silicon dioxide ($SiO_2$) is generally employed to keep performance of a transistor better.

In order to immobilize the nucleic acid probe 6 on the surface of the gate insulator 5, one of the terminal ends of the nucleic acid probe 6 may be chemically modified to have an amino group ($NH_2$ group), thiol group (SH group), biotin, or the like. When the nucleic acid probe 6 that is chemically modified to have an amino group is used, the surface of the gate insulator 5 is modified with aminopropylethoxysilane, polylysine, or the like to introduce amino groups on the surface of the insulating film, and then reacted with glutaraldehyde or phenylene diisocyanate (PDC) to immobilize the nucleic acid probe 6 that has been chemically modified to have an amino group on the surface of the gate insulator 5. When the nucleic acid probe 6 chemically modified to have a thiol group is immobilized on the surface of the gate insulator 5, a gold thin film is formed on the gate insulator 5, and the nucleic acid probe 6 is immobilized by taking advantage of an affinity between thiol group and gold. Furthermore, when the nucleic acid probe 6 chemically modified to have biotin is immobilized, streptoavidin is introduced onto the surface of the gate insulator 5, and the nucleic acid probe 6 is immobilized on the surface of the gate insulator 5 by taking advantage of an affinity between biotin and streptoavidin. At the time of practical immobilization, a solution containing the nucleic acid probe 6 is dropped or spotted only in a predetermined area on the surface of the gate insulator 5, thereby immobilizing the nucleic acid probe 6 only in a desired area on the gate insulator 5.

On the other hand, by forming a fixed carrier on the surface of the gate insulator 5, the nucleic acid probe 6 may be immobilized on the surface or in the inside of the fixed carrier in an indirect way. The materials that can be used for the fixed carrier include agarose, polyacrylamide, polyhydroxyethyl methacrylate (pHEMA), and the like. The fixed carrier may be chemically modified to have amino groups, streptoavidin, or the like, and as described above, the nucleic acid probe may be immobilized on the fixed carrier by using glutaraldehyde or PDC, or by taking advantage of an affinity with avidin, respectively. In this way, the nucleic acid probe 6 may also be immobilized indirectly on the gate insulator 5 of the insulated gate field effect transistor 4 via the fixed carrier.

In the DNA microarray 1 constructed as described above, following application of a sample to be examined, the target gene contained in the sample and the nucleic acid probe 6 are allowed to hybridize to each other under an appropriate reaction condition. That is, a complex of either one of the nucleic acid probe 6 in the first area 3a and the nucleic acid probe 6 in the second area 3b with the target gene is formed depending on the polymorphism of the target gene contained in the sample, or complexes of both of the nucleic acid probe 6 in the first area 3a and the nucleic acid probe 6 in the second area 3b with the target gene are formed.

Under an appropriate pH condition of a buffer solution that is used for hybridization of the sample to be examined, nucleic acids are charged negative. Accordingly, the complex formation between the nucleic acid probe 6 and the target gene induces a change in electric charge density in the vicinity of the gate insulator 5 of the insulated gate field effect transistor 4, thereby allowing the surface potential of the gate insulator 5 to be changed. This change behaves like a gate voltage change of a conventional insulated gate field effect transistor, resulting in a change of conductivity of the channel. Therefore, the complex formation in each nucleic acid probe part 2 can be detected as a change in drain current passing between the source 8 and the drain 9.

Figure 3:
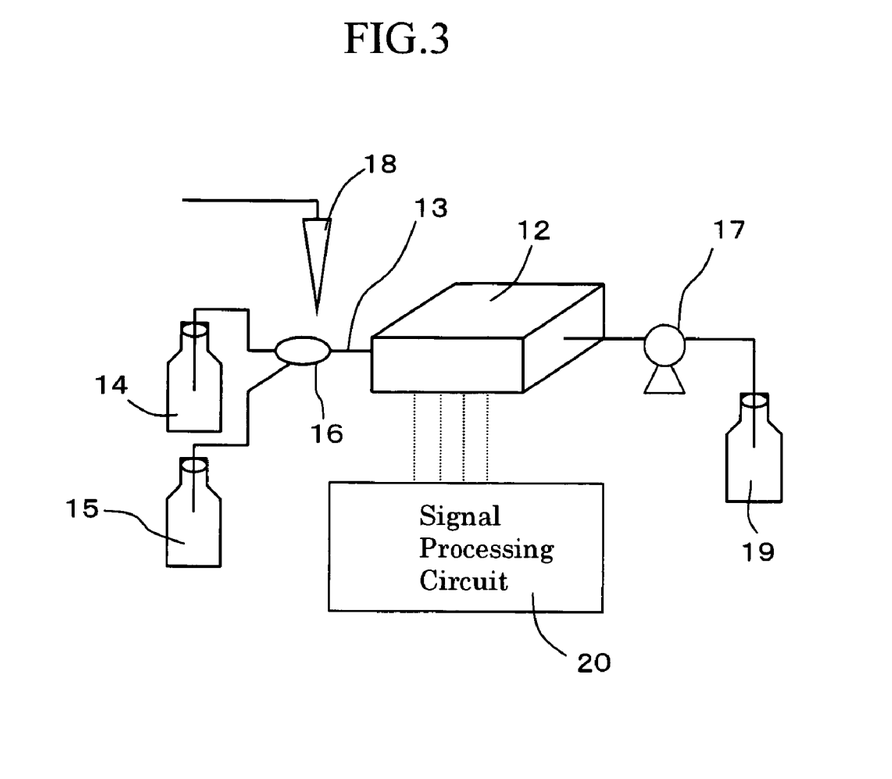
FIG. 3 is a schematic structure showing a nucleic acid detection apparatus to which the present invention is applied.

When the complex formation in each nucleic acid probe part 2 is detected, for example, a detection apparatus 10 as shown in FIG. 3 can be used. The detection apparatus 10 is provided with a flow cell 12 in which the DNA microarray 1 is placed, a flow channel 13 to supply various solutions to the flow cell 12, a hybridization solution 14 and a washing solution 15 that are connected to the leading end of the flow channel 13, a valve 16 that is provided on the flow channel 13 between the hybridization solution 14/the washing solution 15 and the flow cell 12 and used for switching the hybridization solution 14 and the washing solution 15, a pump 17 that controls the supply of each solution to the flow cell 12, a dispenser 18 that supplies a sample, an intercalator, and the like to the flow channel 13 via the valve 16, a waste bottle 19 that is connected to the terminal end of the flow channel 13, and a signal processing circuit 20 that processes and computes outputs from the DNA microarray 1 placed in the flow cell 12.

Figure 4:
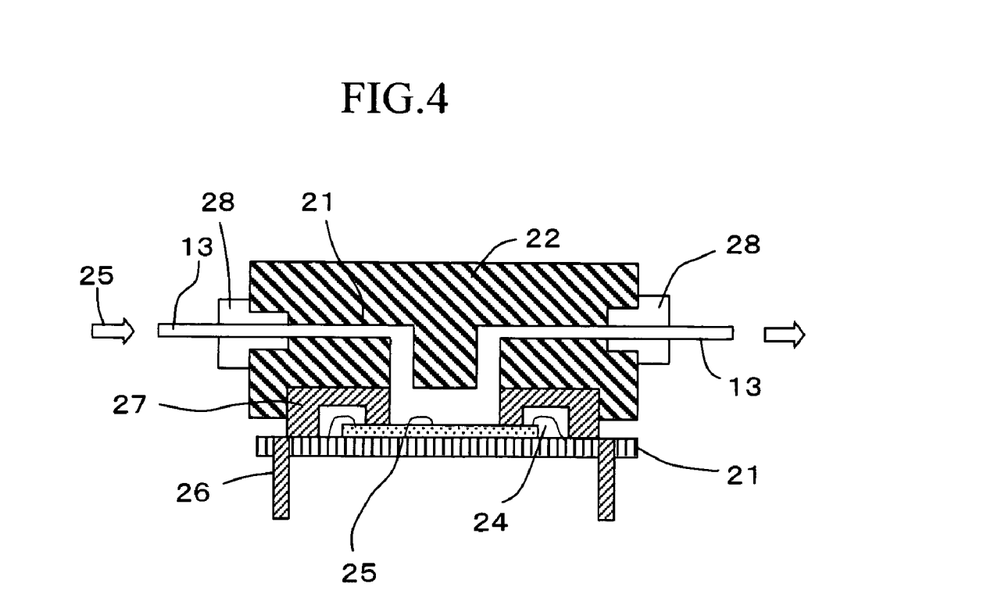
FIG. 4 is a cross sectional view of an essential part of a flow cell.
Figure 5:
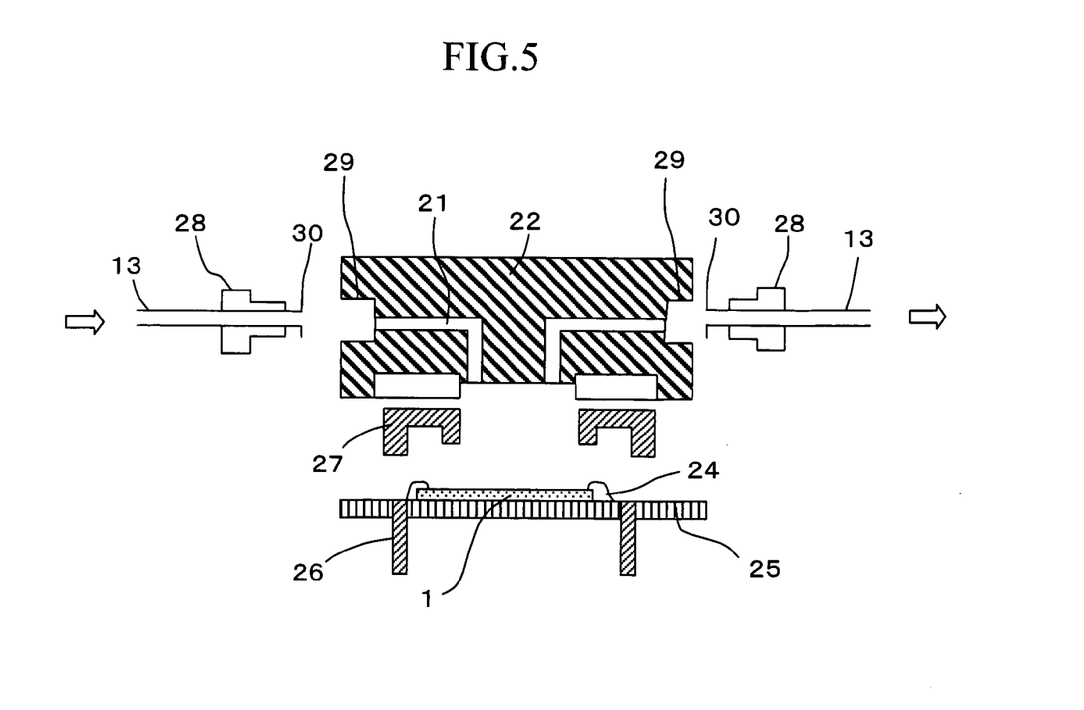
FIG. 5 is an exploded cross sectional view of the essential part of the flow cell.

The flow cell 12 shown in FIG. 4 is provided with a housing 22 in which an internal flow channel 21 is formed, a printed circuit board 25 that is electrically connected to the DNA microarray 1 via wires 24 to serve as signal wires, pins 26 that connect electrically the printed circuit board 25 and the signal processing circuit 20, a protective cap 27 that separates the wires 24 from the internal flow channel 21, and bolts 28 that connect the internal flow channel 21 and the flow channel 13. FIG. 5 is an exploded cross sectional view of the flow cell 12.

The internal flow channel 21 in the housing 22 is provided inside the housing by making, for example, a hole of one millimeter diameter, and makes contact with the DNA microarray 1 at the approximate center of the housing 22. Here, the internal flow channel 21 is in contact with at least the first region 3a and the second region 3b in the DNA microarray 1. Further, the internal flow channel 21 is connected to the flow channel 13 by attaching bolts 28 with the flow channel 13 inside to bolt-mounting portions 29 in the housing 22. The bolt-mounting portions 29 in the housing 22 are threaded so as to be fitted with the bolts 28 to be attached.

The end surface of the flow channel 13 that makes contact with the internal flow channel 21 is treated so as to become flattened. By flattening the end surface of the flow channel 13 that makes contact with the internal flow channel 21, the flow channel 13 and the internal flow channel 21 can be kept in absolute contact with each other when the bolts 28 are screwed in, thereby preventing a solution from leaking.

The printed circuit board 25 is capable of detecting outputs from each of the plurality of the insulated gate field effect transistors 3 that correspond to a plurality of the nucleic acid probe parts 2, respectively, via the wires 24.

The protective cap 26 is made of, for example, acryl, polypropylene, polycarbonate, or the like, and provided between the housing 22 and the printed circuit board 25. The provision of the protective cap 26 between the housing 22 and the printed circuit board 25 prevents the wires 24 from being exposed to the internal flow channel 21.

The detection apparatus 10 constructed as described above makes it possible to identify polymorphisms of a target gene contained in a sample to be examined using the DNA microarray mounted in the flow cell 12. Specifically, first, the valve 16 is switched so as to supply only the hybridization solution 14 to the flow channel 13, and the pump 17 is driven. At the same time, the sample is supplied from the dispenser 18 to the flow channel 13 via the valve 16. This makes it possible to supply the hybridization solution 14 containing the sample to the flow channel 13 and the internal flow channel 21 in the flow cell 12, thereby allowing the sample to interact with the first region 3a and the second region 3b of the DNA microarray 1.

Thus, the nucleic acid probe 6 having a nucleotide sequence complementary to the target gene contained in the sample and the target gene undergo hybridization reaction in the first region 3a or the second region 3b, or in both of the first region 3a and the second region 3b. In other words, the target gene contained in the sample hybridizes only to the nucleic acid probe 6 having a nucleotide sequence complementary to the target gene among the nucleic acid probes 6 contained in the first region 3a and the second region 3b. After the reaction, the solution supplied to the flow channel 13 and the internal flow channel 21 is sent to the waste bottle 19 by the pump 17.

When the nucleic acid probe 6 and the target gene hybridize to each other (complex formation) in the detection apparatus 10, it is reflected as a change in drain current appearing in the insulated gate field effect transistors 3. In the detection apparatus 10, the change in drain current in the insulated gate field effect transistors 3 is detected by the printed circuit board, and signals are output to the signal processing circuit 20. Particularly, since the detection apparatus 10 is provided with plural nucleic acid probe parts 2, plural signals from each of the plural insulated gate field effect transistors 3 are output to the signal processing circuit 20.

Figure 6:
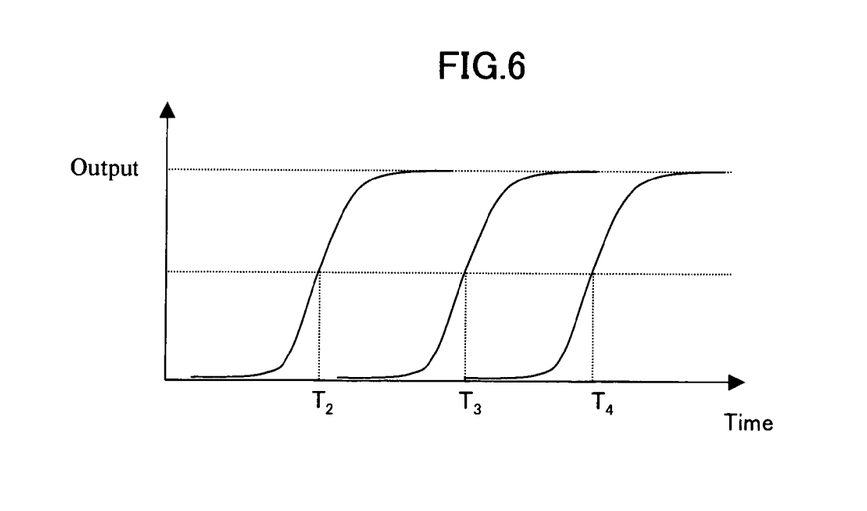
FIG. 6 is a characteristic diagram showing outputs from a plurality of nucleic acid probe parts.

At this time, the plural nucleic acid probe parts 2 bring about time differences in hybridization between the nucleic acid probe 6 and the target gene. This results in time differences in signal outputs from the plural insulated gate field effect transistors 4 as well. For example, signals from three insulated gate field effect transistors 4 are output at different times, respectively, as shown in FIG. 6.

The signal processing circuit 20 measures time taken to reach a threshold level for each of the plural signals output at different times from the plural insulated gate field effect transistors 4, and determines the frequency distribution using time as the horizontal axis and the number of pieces of the nucleic acid probe parts 2 whose outputs have been measured to exceed the threshold level as the vertical axis. The signal processing circuit 20 determines an average value in the frequency distribution obtained for the plural nucleic acid probe parts 2 as an output time.

Figure 7:
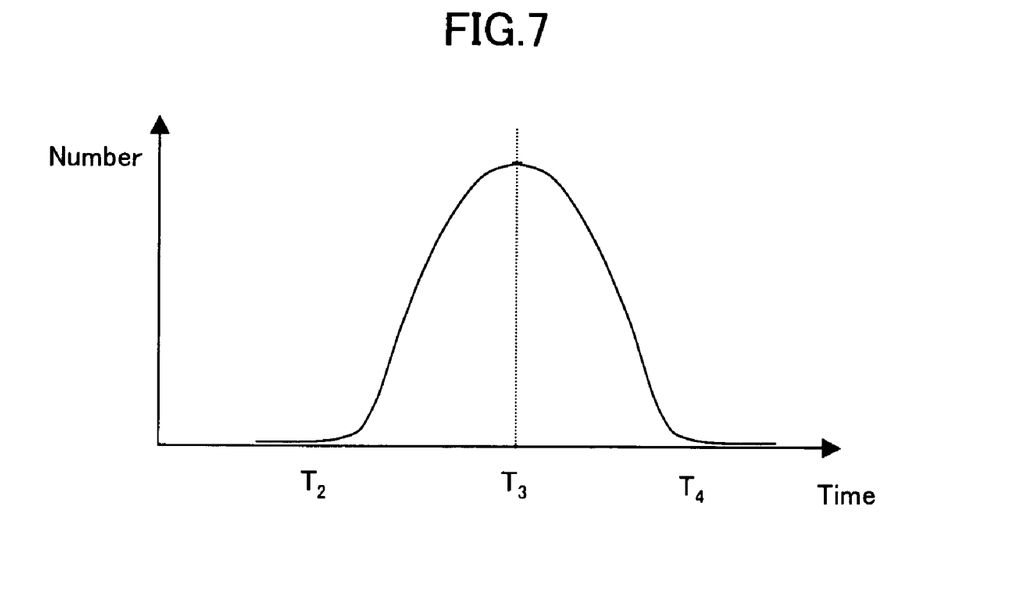
FIG. 7 is a characteristic diagram showing a result after processing by a signal processing circuit based on the outputs from the plurality of nucleic acid probe parts.

When the frequency distribution is determined using measured time as the horizontal axis and the number of pieces of the nucleic acid probe parts 2 whose outputs have been measured to exceed the threshold level as the vertical axis, a normal distribution is obtained, for example, as shown in FIG. 7. In this case, the signal processing circuit 20 determines the output time $T_3$ as an average value (a maximum value in the normal distribution in this case) of the frequency distribution. The signal processing circuit 20 is able to determine the output time for the plural nucleic acid probe parts 2 contained in the first region 3a and the output time for the plural nucleic acid probe parts 2 contained in the second region 3b.

The detection apparatus 10 is capable of judging the polymorphisms of the target gene based on each output time from the first region 3a and the second region 3b. That is, when the target gene is a homotype consisting only of a first polymorphism, the output time can be obtained only from the first region 3a. In contrast, when the target gene is a homotype consisting of only a second polymorphism, the output time can be obtained only from the second region 3b. Further, when the target gene is a heterotype consisting of the first polymorphism and the second polymorphism, the output time can be obtained from both of the first region 3a and the second region 3b. As described above, the polymorphism of the target gene can be judged from the output times from the first region 3a and the second region 3b using the detection apparatus 10.

By virtue of the detection apparatus 10, a measurement error can be made small compared to when the polymorphism is judged by a single nucleic acid probe part, thereby allowing more accurate judgment to be made.

The detection apparatus 10 allows the polymorphism of the target gene to be determined not only by obtaining the output time by the signal processing circuit 20 as described above, but also by the following way. The signal processing circuit 20 computes proportions of the insulated gate field effect transistors 4 that have output signals after a predetermined elapsed time for each of the first region 3a and the second region 3b and compares them to each other. As the result, when the proportion for the first region 3a is larger compared to that for the second region 3b, the target gene can be judged to be a homotype consisting of only the first polymorphism. Conversely, when the proportion for the second region 3b is larger compared to that for the first region 3a, the target gene can be judged to be a homotype consisting of only the second polymorphism. Further, when the proportion for the first region 3a and that for the second region 3b are comparable, the target gene can be judged to be a heterotype consisting of the first polymorphism and the second polymorphism.

It should be noted that when the presence of the first polymorphism, for example, is desired to be promptly detected, the first polymorphism of interest may be judged to be present at the time when an output from at least one nucleic acid probe part 2 among the nucleic acid probe parts 2 contained in the first region 3a has been obtained. This way of judging makes it possible to judge promptly whether or not the first polymorphism is contained in the sample.

Figure 8:
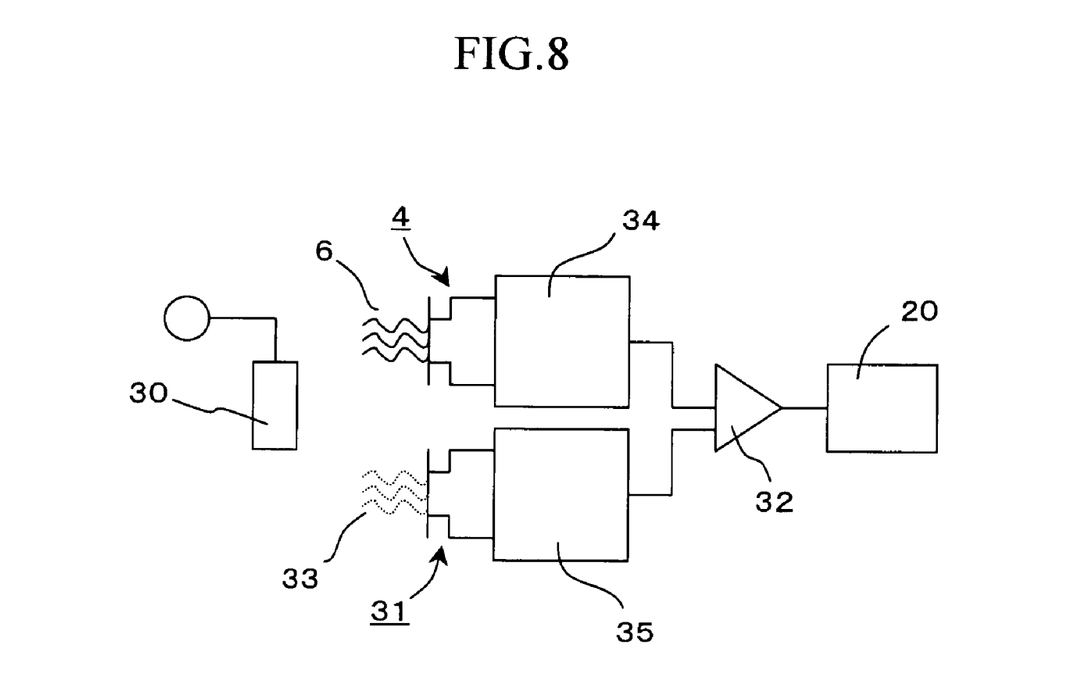
FIG. 8 is a circuit diagram showing a case where the outputs from the plurality of nucleic acid probe parts are measured with the use of a reference field effect transistor.

Alternatively, the detection apparatus 10 may be provided with a reference electrode 30, a reference field effect transistor 31, and a differential measurement circuit 32 that measures a differential output between an output from the insulated gate field effect transistor 4 and an output from the reference field effect transistor 31. In this case, a nucleic acid 33 that does not contain a nucleotide sequence complementary to the target gene is immobilized on the surface of the gate insulator of the reference field effect transistor 31. Thus, the nucleic acid immobilized on the surface of the gate insulator of the reference field effect transistor 31 does not hybridize to the target gene.

The reference electrode 30 is, for example, formed by dipping a silver-silver chloride electrode or a calomel electrode into an internal solution having a specified composition and concentration, and is provided at a place in contact with a solution supplied to the internal flow channel 21. The reference electrode 30 may be provided, for example, inside the flow cell 21.

In the detection apparatus 10 constructed in this way, a change in drain current of the insulated gate field effect transistor 4 is detected as a surface potential by a drive circuit 34, and a change in drain current of the reference field effect transistor 31 is detected as a surface potential by a drive circuit 35. The differential measurement circuit 32 measures the difference of the respective surface potentials of the drive circuit 34 and the drive circuit 35, and inputs the difference to the signal processing circuit 20 as a signal from the insulated gate field effect transistor 4.

Owing to outputting of a signal from the insulated gate field effect transistor 4 by such differential measurement, changes in output values occurring from differences in electric properties of each insulated gate field effect transistor and those due to ambient temperature and light changes can be compensated. Further, changes in output values arising from non-specific adsorption of charged particles in the sample on the gate insulator 5 can be offset. In this way, only the output change caused by hybridization of the target gene and the nucleic acid probe 6 can be accurately detected by the detection apparatus 10.

It is desirable that the reference field effect transistor 31 and the insulated gate field effect transistor 4 are integrated on the same substrate. Integrating the reference field effect transistor 31 and the insulated gate field effect transistor 4 on the same substrate allows electric properties of the insulated gate field effect transistor 4 and the reference field effect transistor 31 to be uniformed.

In addition, the detection apparatus 10 does not require the same number of the reference field effect transistors 31 as that of the insulated gate field effect transistors 4. Since one reference field effect transistor 31 is used in common when outputs from the plural insulated gate field effect transistors 4 are obtained, provision of at least one reference field effect transistor 31 may suffice.

Further, the surface potentials of the reference field effect transistor 31 and the insulated gate field effect transistor 4 can be stably measured by using the reference electrode 30 as a standard for the potential measurement.

In the detection apparatus 10 described above, it is also possible to quantify the target gene in the sample. When the target gene in the sample is quantified, similar measurements are performed with the use of plural samples containing known concentrations of the target gene in advance, and the output times are determined for these plural samples. The target gene contained in the sample to be measured can be quantified by comparing the output time of the measured sample to each output time of the plural samples.

In this case, particularly, the output time is measured by using the plural nucleic acid probe parts 2, and therefore, an error in quantitative determination arising from noise components, for example, due to non-specific hybridization of the target gene can be corrected. Accordingly, the target gene contained in the sample to be measured can be quantified with high accuracy by the detection apparatus 10.

Figure 9:
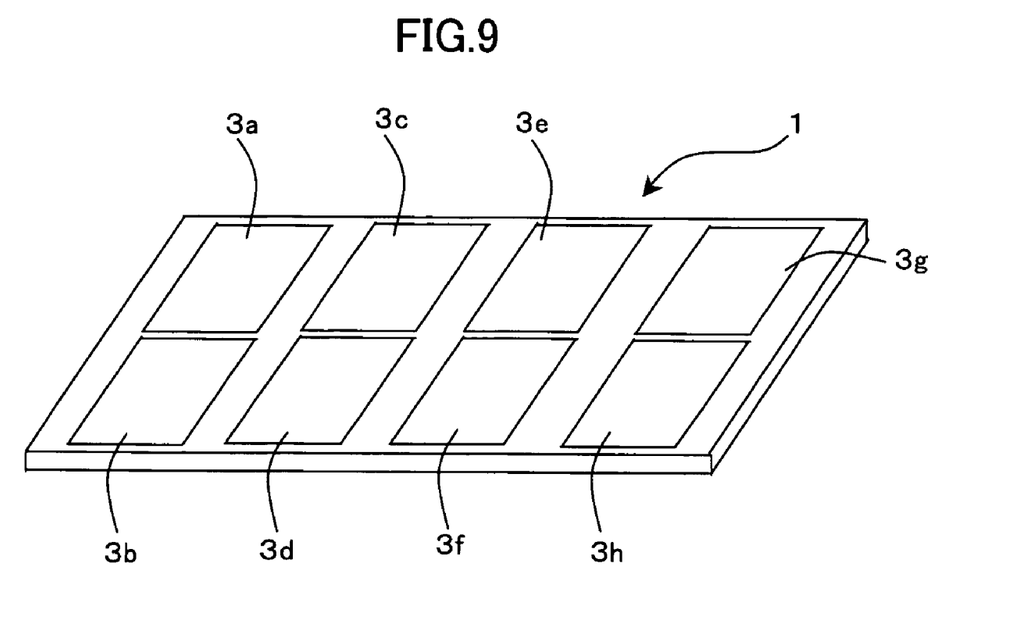
FIG. 9 is a schematic perspective view of another example of the DNA microarray to which the present invention is applied.

Furthermore, the detection apparatus 10 may use the DNA microarray 1 provided with a first section consisting of the first region 3a and the second region 3b, a second section consisting of a third region 3c and a fourth region 3d, a third section consisting of a fifth region 3e and a sixth region 3f, and a fourth section consisting of a seventh region 3g and an eighth region 3h. The first region 3a to the eighth region 3h are provided with the plural nucleic acid probe parts 2, respectively. The nucleic acid probe 6 that hybridizes to the first polymorphism of the target gene is immobilized in the first region 3a, the third region 3c, the fifth region 3e, and the seventh region 3g. The nucleic acid probe 6 that hybridizes to the second polymorphism of the target gene is immobilized in the second region 3b, the fourth region 3d, the sixth region 3f, and the eighth region 3h.

In addition, the time required for hybridization between the nucleic acid containing the target gene and the nucleic acid probes 6 is adjusted so as to be mutually different in the first, second, third, and fourth sections. Specifically, the time required for hybridization in each section becomes different by making mutually different the immobilization densities of the nucleic acid probe 6 in the first section, the nucleic acid probe 6 in the second section, the nucleic acid probe 6 in the third section, and the nucleic acid probe 6 in the fourth section. Further, the time required for hybridization in each section becomes different by making different the areas of the nucleic acid probe parts 2 in the first section, the nucleic acid probe parts 2 in the second section, the nucleic acid probe parts 2 in the third section, and the nucleic acid probe parts 2 in the fourth section. Still further, the time required for hybridization in each section becomes different by making different the lengths (nucleotide lengths) of the nucleic acid probe 6 in the first section, the nucleic acid probe 6 in the second section, the nucleic acid probe 6 in the third section, and the nucleic acid probe 6 in the fourth section.

When the DNA microarray 1 shown in FIG. 9 is used, the output time is measured for each of the first to the fourth sections by the signal processing circuit 20. Since the time required for hybridization is different in the first to the fourth sections, it is possible to select an optimal section from the measured output times. In other words, when the time taken for hybridization between nucleic acid containing the target gene and the nucleic acid probe 6 is too short or too long, an error in quantifying the target gene becomes large. Accordingly, a highly accurate quantitative determination can be carried out by selecting an optimum section and measuring the output time using signals from the nucleic acid probe parts 2 contained in the selected section.

It should be noted that when the presence of the first polymorphism is desired to be promptly detected also in the case of using the DNA microarray 1 shown in FIG. 9, the first polymorphism may be judged to be present at the time when an output from at least one nucleic acid probe part 2 among the nucleic acid probe parts 2 contained in any one of the regions consisting of the first region 3a, the third region 3c, the fifth region 3e, and the seventh region 3g has been obtained. When the DNA microarray 1 shown in FIG. 9 is used, it is possible to judge promptly whether or not the first polymorphism is contained in the sample.

SECOND EMBODIMENT

For a second embodiment, a system to detect whether or not a target gene is contained in a sample is explained. At the same time, when the target gene is contained in the sample, a system to quantify the target gene is explained.

In the second embodiment, a DNA microarray in which the 5' terminus of the nucleic acid probe 6 having a nucleotide sequence complementary to the target gene to be detected in the 3' terminal portion is immobilized on the surface of the gate insulator 2 is used for the DNA microarray 1.

In the present embodiment, a solution containing human chromosomes extracted from tissue pieces and white blood cells can be used as a sample. Particularly, in the present embodiment, nucleic acid amplification is carried out on a plurality of the nucleic acid probe parts 2, respectively, using the immobilized nucleic acid probe 6 as a primer and a human chromosome contained in the sample of interest as a template, and the nucleic acid amplification is monitored by a plurality of the corresponding insulated gate field effect transistors 4.

Specifically, the valve 16 is switched first such that reagents necessary for the nucleic acid amplification can be supplied to the flow channel 13, and the pump 17 is driven. At the same time, a solution containing human chromosomes is supplied from the dispenser 18 to the flow channel 13 via the valve 16. In this way, the solution containing human chromosomes and the reagents necessary for the nucleic acid amplification can be supplied to the flow channel 13 and the internal flow channel 21 of the flow cell 12.

Figure 10:
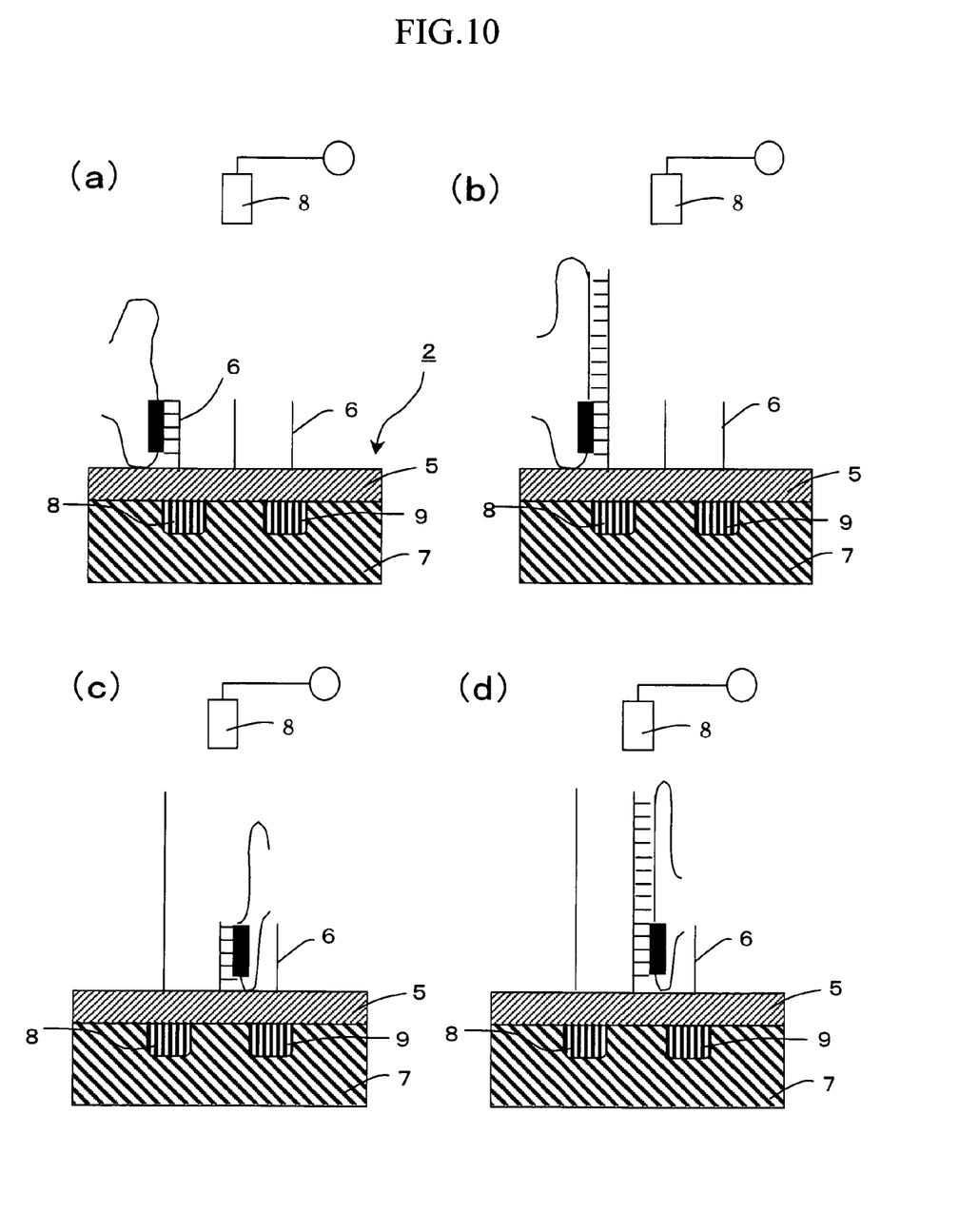
FIG. 10 is a schematic cross sectional view of the essential part of the DNA microarray showing each step of nucleic acid amplification carried out on the DNA micro array.

Next, nucleic acid amplification is carried out on the DNA microarray 1. As specifically shown in FIGS. 10A to 10D, when a DNA fragment 38 having the target gene is contained in the solution containing human chromosomes, the nucleic acid amplification is performed using the nucleic acid probe 6 as a primer. That is, first as shown in FIG. 10A, hybridization (annealing) between the nucleic acid probe 6 and a portion of the target gene in the DNA fragment 38 takes place by controlling the gate insulator 2 to a predetermined temperature. Then, as shown in FIG. 10B, an extension reaction is carried out from the 3' terminus of the nucleic acid probe 6 using the DNA fragment 38 as the template with the aid of an enzyme (DNA polymerase, etc.) included in the reagents necessary for the nucleic acid amplification by controlling the gate insulator 2 to a predetermined temperature. Controlling the gate insulator 2 to a predetermined temperature after the extension reaction induces heat denaturation to allow the DNA fragment 38 to be dissociated. Then again, by controlling the gate insulator 2 to the predetermined temperature, hybridization (annealing) between the unreacted nucleic acid probe 6 and the portion of the target gene in the DNA fragment 38 takes place as shown in FIG. 10C. Subsequently, as shown in FIG. 10D, the extension reaction takes place from the 3' terminus of the nucleic acid probe 6 using the DNA fragment 38 as the template with the aid of the enzyme (DNA polymerase, etc.) included in the reagents necessary for the nucleic acid amplification by controlling again the gate insulator 2 to the predetermined temperature.

In this way, the extension reaction from the 3' terminus of the nucleic acid probe 6 using the DNA fragment 38 as the template is carried out in turn by controlling the temperature of the gate insulator 2. When the DNA fragment 38 having the target gene is contained in the sample to be measured, the progress of the extension reaction in the nucleic acid probe part 2 results in a change of charge density in the vicinity of the gate insulator 5 of the insulated gate field effect transistors 4 corresponding to the nucleic acid probe part 2, and the surface potential of the gate insulator 5 is changed. This change acts like a gate voltage change in a conventional insulated gate field effect transistor, resulting in a change of electric conductivity of the channel. Therefore, the progress of the extension reaction in each nucleic acid probe part 2 can be detected as a change in drain current flowing between the source 8 and the drain 9 by using the detection apparatus 10.

In the present embodiment as well, a measurement error is minimized owing to the use of plural nucleic acid probe parts 2 when compared to the case in which the target gene is detected by a single nucleic acid probe part, thereby allowing the target gene to be accurately detected even when its amount present in a sample is small.

Incidentally, the detection apparatus 10 described above makes it possible to quantify the target gene in the sample. When the target gene in the sample is quantified, a plurality of samples containing known concentrations of the target gene are measured beforehand in a similar way, and the output time is determined for each of these plural samples. The target gene contained in a sample to be measured can be quantified by comparing the output time of the measured sample and each output time of the plural samples.

In this case, particularly, an error in the quantitative determination, for example, due to noise components arising from non-specific hybridization of the target gene can be corrected since the output time is measured by using the plurality of the nucleic acid probe parts 2. Therefore, the target gene contained in the sample to be measured can be quantified by the detection apparatus 10 with high accuracy.

Specific examples are shown below.

In a first specific example, the following nucleic acid probe 6 with the 5' terminus modified to have an amino group was immobilized on the gate insulator 5 of the insulated gate field effect transistor 4 in order to examine the presence or absence of hepatitis B virus DNA.

HBV probe (i);
(SEQ ID NO: 1)
5'-GCG GAT CCG TGG AGT TAC TCT CGT TTT TGC-3'.

The nucleic acid 33 having a sequence different from the HBV probe (i), e.g. the nucleic acid 33 having a length of 30 nucleotides composed exclusively of A, was immobilized on the gate insulator of the reference field effect transistor 31. Here, the nucleic acid 33 may not be immobilized on the gate insulator of the reference field effect transistor 31, but may be modified to have an amino group on the 5' terminus.

The sample used was Hepatitis B virus DNA extracted from serum that is available in a kit (Qiagen viral DNA kit). One hundred microliter of a sample solution containing the Hepatitis B virus DNA, 1× PCR buffer ($Mg^{2+}$ plus) (product of Takara Co., Ltd.), 0.4 μM dNTP, and 5 units of Taq polymerase (Takara) was introduced into the flow cell 12 from the dispenser 18, and the gate insulator 5 was heated and cooled according to the following steps (1) to (3):

(1) Heat denaturation; 94° C. for 3 min
(2) A cycle of 94° C. for 30 sec for heat denaturation, 55° C. for 30 sec for annealing, and 72° C. for 30 sec for extension reaction is repeated 40 cycles.
(3) Extension reaction; 72° C. for 10 min After completing the above steps (1) to (3), double-stranded nucleic acids were denatured to convert to single-stranded nucleic acids either by raising the temperature of the gate insulator 5 or introducing an alkaline solution into the flow cell 12 from the dispenser 18. Then, a washing solution was introduced into the flow cell 12 from the dispenser 18, thereby removing nucleic acids not immobilized on the substrate, unreacted nucleic acids, and various components from the DNA microarray 1. Subsequently, a buffer solution was introduced into the flow cell 12 from the dispenser 18, and output values from the insulated gate field effect transistors 4 were measured by the signal processing circuit 20.

Figure 11:
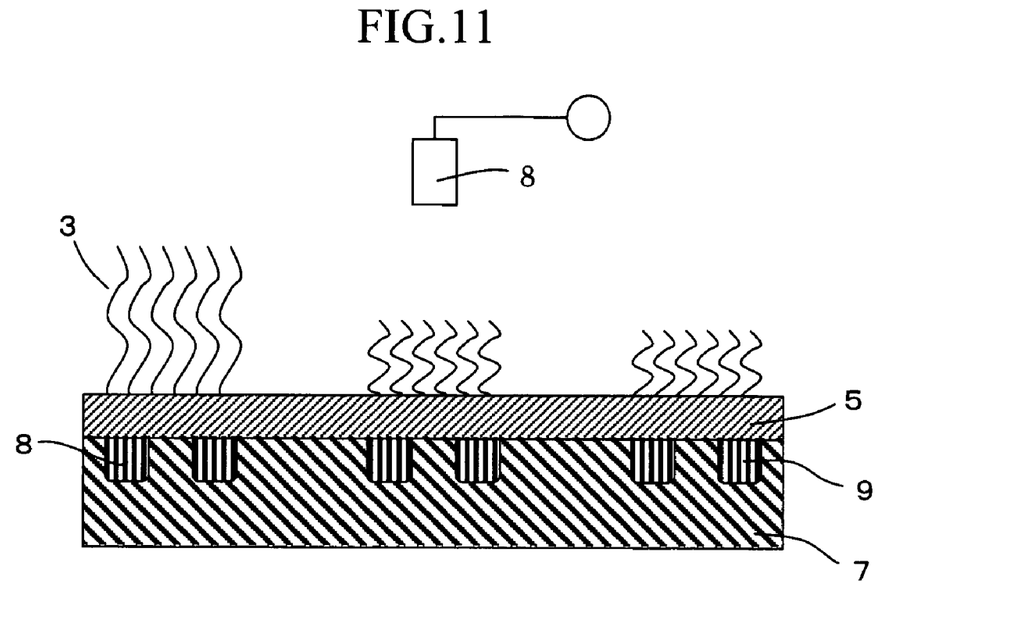
FIG. 11 is a schematic cross sectional view of the essential part of the DNA microarray showing a state that a single-stranded nucleic acid is extended from a nucleic acid probe.

In the first specific example, the output values from the signal processing circuit 20 were the ones resulting from the single-stranded nucleic acids extended from the 3' terminus of the HBV probe (i) by the nucleic acid amplification, and the detection was made possible by a larger number of nucleotides compared with that of the nucleic acid 33 immobilized on the gate insulator of the reference field effect transistor 31. FIG. 11 schematically depicts a state that single-stranded nucleic acids were extended from the nucleic acid probe 6 and the nucleic acid 33 immobilized on the gate insulator of the reference field effect transistor 31.

When the sample containing Hepatitis B virus DNA was used, the differential output of surface potential between the insulated gate field effect transistor 4 and the reference field effect transistor 31 was 2.8 mV in the first specific example. On the other hand, when a sample not containing Hepatitis B virus DNA was used, the differential output measured in a similar manner was 0.4 mV. From these results, a significant difference between the sample containing Hepatitis B virus DNA and the sample not containing Hepatitis B virus DNA was obtained.

In a second specific example, the nucleic acid probe 6 having a tendency to assume a higher order structure in accordance with the progress of the amplification reaction that takes place by the presence of the target gene in the sample was immobilized on the gate insulator 5 of the insulated gate field effect transistor 4 in order to detect the presence or absence of hepatitis B virus DNA with high sensitivity. The nucleic acid probe 6 used in the second specific example had a nucleotide sequence complementary to Hepatitis B virus DNA, with its 5' terminus being modified to have an amino group. The nucleic acid probe 6 was as follows:

HBV probe (ii);
(SEQ ID NO: 2)
5'-CAT AGC AGC AGG ATG AAG AGG AAT ATG ATA GGA TGT GTC TGC GGC GTT T-3'.

In this example as well, the nucleic acid 33 having a sequence different from the HBV probe (ii), e.g. the nucleic acid 33 having a length of 30 nucleotides composed exclusively of A, was immobilized on the gate insulator of the reference field effect transistor 31.

In the second specific example as well, the above described steps (1) to (3) were carried out under the same reaction conditions using the same reagents as those in the first specific example. Then, nucleic acids not immobilized on the substrate, unreacted nucleic acids, and various components were removed from the DNA microarray 1, and output values were measured by the signal processing circuit 20.

Figure 12:
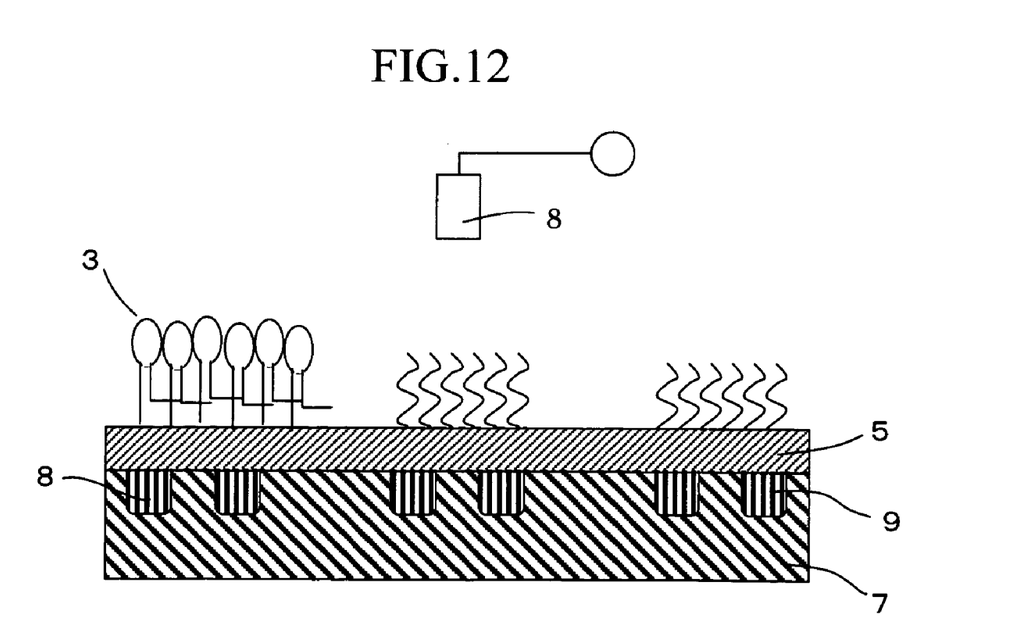
FIG. 12 is a schematic cross sectional view of the essential part of the DNA microarray showing a higher order structure formed by the single-stranded nucleic acid that is extended from the nucleic acid probe.

In the second specific example, the output values were the ones resulting from the single-stranded nucleic acids that extended from the 3' terminus of the HBV probe (ii) by the nucleic acid amplification and formed a higher order structure. The detection was made possible by a larger number of nucleotides compared with that of the nucleic acid 33 immobilized on the gate insulator of the reference field effect transistor 31 as well as by the difference in the higher order structure. FIG. 12 schematically depicts a state that single-stranded nucleic acids were extended from the nucleic acid probe 6 and the nucleic acid 33 immobilized on the gate insulator of the reference field effect transistor 31. In the second specific example, when Hepatitis B virus DNA was contained in the sample, the 3' terminus of the nucleic acid probe 6 assumes a higher order structure, i.e. a stem structure or a loop structure in this case, as the result of the progress of the extension reaction, as shown in FIG. 12. This stem structure is formed because the single-stranded nucleic acid synthesized by the extension reaction is complementary to the HBV probe (ii) from its 5' terminus up to the 30 nucleotides. Further, the loop structure is formed by the 19 nucleotides of the HBV probe (ii) on its 3' terminal side.

When the sample containing Hepatitis B virus DNA was used, the differential output of surface potential between the insulated gate field effect transistor 4 and the reference field effect transistor 31 was 4.8 mV in the second specific example. On the other hand, when a sample not containing Hepatitis B virus DNA was used, the differential output measured in a similar manner was 0.5 mV. From these results, a significant difference between the sample containing Hepatitis B virus DNA and the sample not containing Hepatitis B virus DNA was obtained. Furthermore, since the nucleic acid probe 6 formed a higher order structure as the result of the extension reaction in the second specific example, the output value was obtained with higher sensitivity compared with that in the first specific example.

Next, as a third specific example, the following nucleic acid probes 6 modified to have an amino group at the 5' terminus were immobilized on the gate insulator 5 of the insulated gate field effect transistor 4 in order to detect the presence or absence of hepatitis B virus DNA with two kinds of the probes:

HBV probe (i);
(SEQ ID NO: 1)
5'-GCG GAT CCG TGG AGT TAC TCT CGT TTT TGC-3'

HBV probe (iii);
(SEQ ID NO: 3)
5'-GCA AGC TTT CTA ACA ACA GTA GTT TCC GG-3'

The nucleic acid 33 having a sequence different from the HBV probe (ii), e.g. the nucleic acid 33 having a length of 30 nucleotides composed exclusively of A, was immobilized on the gate insulator of the reference field effect transistor 31.

Figure 13:
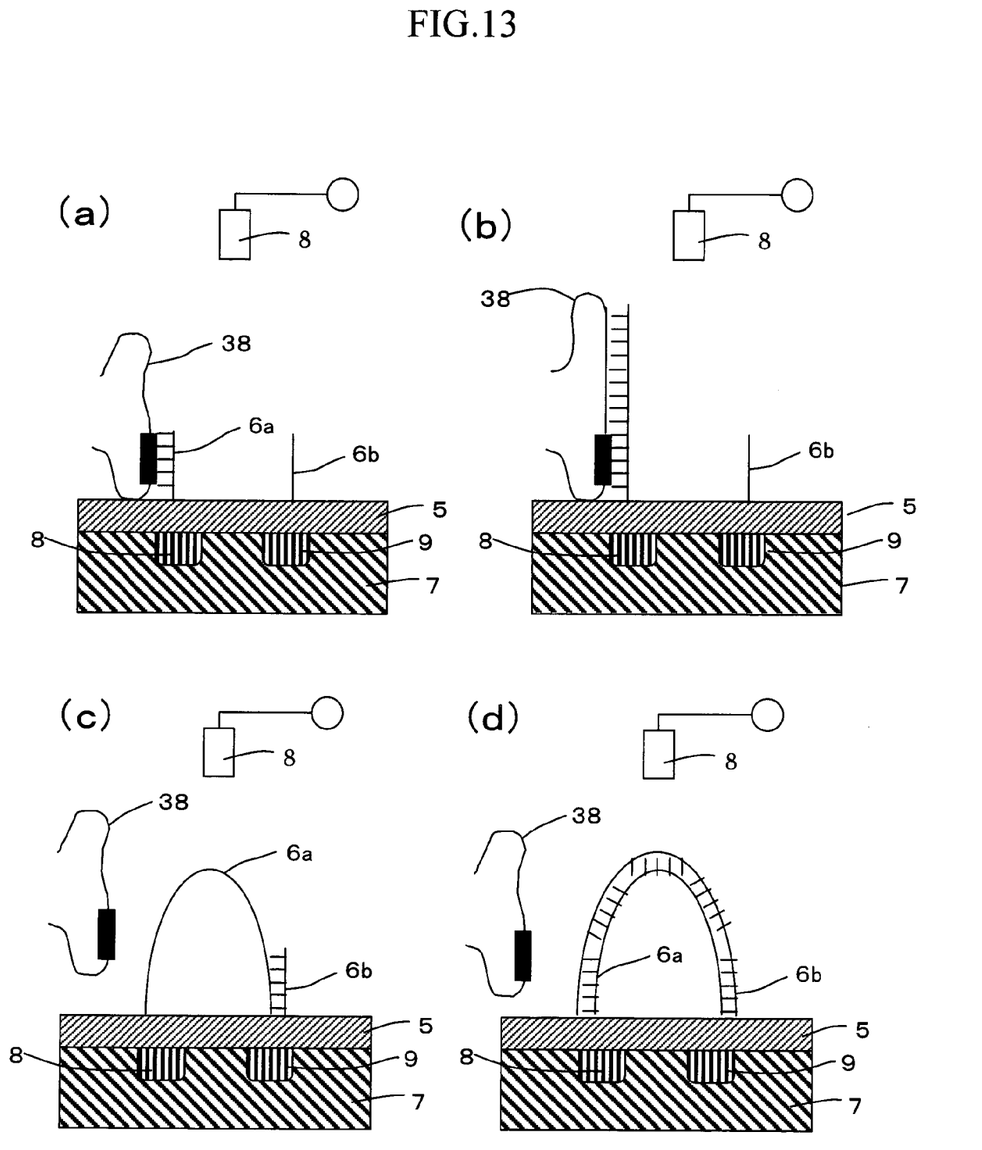
FIG. 13 is a schematic cross sectional view of the essential part of the DNA microarray showing each step carried out at the time when a nucleic acid is detected on the DNA microarray with the use of two kinds of probes.

In the third specific example as well, the above described steps (1) to (3) were carried out under the same reaction conditions using the same reagents as those in the first specific example. FIGS. 13A to 13D illustrate the nucleic acid amplification in the third specific example. In FIGS. 13A to 13D, the HBV probe (i) is denoted by a nucleic acid probe 66a and the HBV probe (iii) is denoted by a nucleic acid probe 6b. When the sample to be studied contained hepatitis B virus DNA, hybridization (annealing) took place between the DNA fragment 38 containing hepatitis B virus DNA and the nucleic acid probe 6a by controlling the gate insulator 2 to the first predetermined temperature as shown in FIG. 13A. Next, as shown in FIG. 13B, an extension reaction was carried out from the 3' terminus of the nucleic acid probe 6a using the DNA fragment 38 as the template with the aid of an enzyme (DNA polymerase, etc.) included in the reagents necessary for nucleic acid amplification by controlling the gate insulator 2 to the second predetermined temperature. Controlling the gate insulator 2 to the third temperature induced heat denaturation to allow the DNA fragment 38 to be dissociated, and a portion of the region that extended from the 3' terminus of the nucleic acid probe 6a hybridized (annealed) to the nucleic acid probe 6b as shown in FIG. 13C. Then again, by controlling the gate insulator 2 to the second predetermined temperature, an extension reaction proceeded from the 3' terminus of the nucleic acid probe 6b using the region that extended from the 3' terminus of the nucleic acid probe 6a as the template, and finally nucleic acid double strand was formed between the nucleic acid probe 6a and the nucleic acid probe 6b as shown in FIG. 13D.

Figure 14:
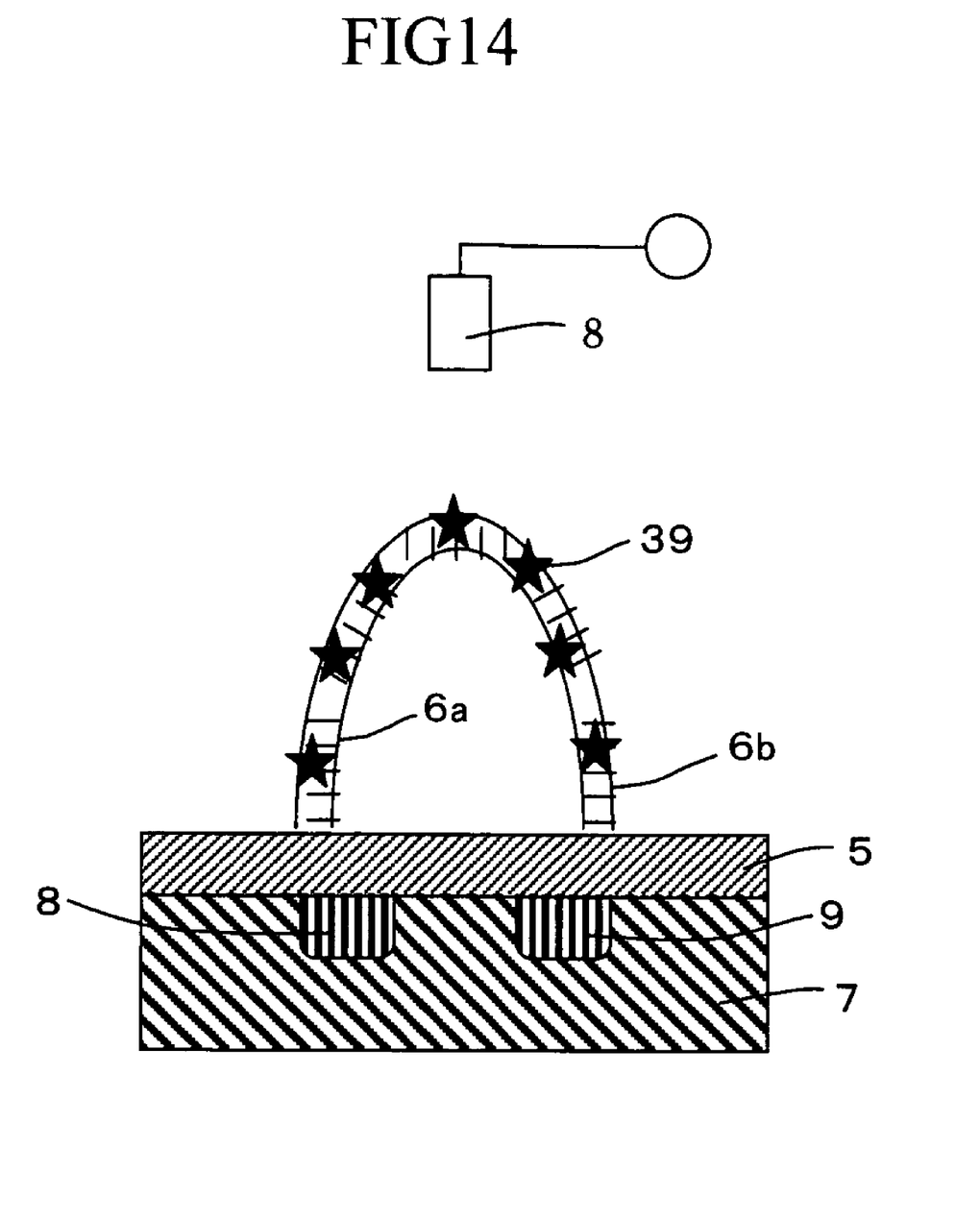
FIG. 14 is a cross sectional view of the essential part of the DNA microarray showing a state treated with an intercalator.

Next, the buffer solution was introduced from the dispenser 18 into the flow channel 13 through the valve 16 to remove the unreacted sample and the like on the DNA microarray 1. Then, a solution containing an intercalator 39 such as ethidium bromide or Hoechst 33258 was introduced from the dispenser 18 into the flow channel 13 through the valve 16, thereby inserting the intercalator 39 into the double stranded nucleic acid of the nucleic acid probe 6a and the nucleic acid probe 6b. The intercalator 39 reacts only with the double stranded nucleic acid to bind, and does not bind to single stranded nucleic acids. After inserting the intercalator 39 into the nucleic acid double strand, an output value was measured by the signal processing circuit 20 in a manner similar to that in the first specific example.

As the result, the differential output was 5.6 mV when the sample containing hepatitis B virus DNA was used. The differential output was 0.4 mV when the sample not containing hepatitis B virus DNA was used. As just described, a significant difference between the sample containing hepatitis B virus DNA and the sample not containing hepatitis B virus DNA was also obtained in the third specific example. On the other hand, the differential output was 2.2 mV when measured in the state of the double stranded nucleic acid without using the intercalator 39 as shown in FIG. 13D. This result indicates that about twofold higher sensitivity could be achieved by the effect of the solution containing the intercalator 39 due to charge originating from the intercalator 39.

As a fourth specific example, the following nucleic acid probes 6 modified to have an amino group at the 5' terminus were immobilized on the gate insulator 5 of the insulated gate field effect transistor 4 in order to detect the presence or absence of hepatitis B virus DNA using two kinds of the probes and a DNA polymerase with strand displacement activity:

HBV probe (ii);

(SEQ ID NO: 2)
5'-CAT AGC AGC AGG ATG AAG AGG AAT ATG ATA GGA TGT GTC TGC GGC GTT T-3'

HBV probe (iv);

(SEQ ID NO: 4)
5'-TCC TCT AAT TCC AGG ATC AAC AAC AAC CAG AGG TTT TGC ATG GTC CCG TA-3'

In the present example, one hundred microliter of a sample solution containing hepatitis B virus DNA, 0.1 mM dNTP, 0.5 mM MgCl$_2$, and 32 units of Bst polymerase (product of New England BioLabs Inc.) was introduced from the dispenser 18 into the flow cell 12, and the gate insulator 5 was incubated at 65° C. to subject to an isothermal amplification reaction. This isothermal amplification reaction proceeds in a manner similar to that shown in FIGS. 10A to 10D. In the present example too, the output value was measured by the signal processing circuit 20 after inserting the intercalator 39 into the nucleic acid double strand in a manner similar to that in the third specific example.

As a result, the differential output was 5.8 mV when the sample containing hepatitis B virus DNA was used. On the other hand, the differential output was 0.3 mV when the sample not containing hepatitis B virus DNA was used. Thus, a significant difference was obtained between the sample containing hepatitis B virus DNA and the sample not containing hepatitis B virus DNA in the fourth specific example as well. On the other hand, the differential output was 2.4 mV when the output value was measured in the state without using the intercalator 39. This result indicated that about twofold higher sensitivity could be achieved by the effect of the solution containing the intercalator 39.

INDUSTRIAL APPLICABILITY

As explained above in detail, in the present invention, the target nucleic acid can be detected as well as quantified by monitoring the outputs from a plurality of the nucleic acid probe parts to determine distribution per unit time with respect to the number of pieces of the nucleic acid probe parts whose outputs exceed a predetermined value. According to the present invention, the target nucleic acid can be detected with high accuracy as well as can be quantified with high accuracy.

The invention claimed is:

1. A method of detecting nucleic acid by using DNA microarrays, comprising the steps of:
   allowing a sample containing nucleic acids to interact with the DNA microarray comprising a plurality of nucleic acid probe parts having a nucleic acid probe capable of hybridizing to a specific nucleic acid;
   monitoring outputs from each of the plurality of nucleic acid probe parts due to hybridization between the nucleic acid probe and the specific nucleic acid to determine distribution per unit time with respect to the number of pieces of the nucleic acid probe parts whose outputs exceed a predetermined value; and
   quantifiying the specific nucleic acid contained in the sample based on a maximum value determined by normalizing the distribution obtained in the above step.

2. The method of detecting nucleic acid by using DNA microarrays according to claim 1, wherein the DNA microarray is formed by immobilizing the nucleic acid probe on the surface of gate insulator directly or via a carrier and comprises a plurality of insulated gate field effect transistors corresponding to the plurality of nucleic acid probe parts; and the outputs from the insulated gate field effect transistors are monitored.

3. The method of detecting nucleic acid by using DNA microarrays according to claim 1, wherein, in the step of allowing the sample containing nucleic acids to interact with the DNA microarray, nucleic acid amplification is carried Out on the DNA microarray using the nucleic acid as a template.

4. The method of detecting nucleic acid by using DNA microarrays according to claim 3, wherein the nucleic acid amplification is carried out by an isothermal amplification method.

* * * * *

SEQUENCE LISTING

```
<160> NUMBER OF SEQ ID NOS: 4

<210> SEQ ID NO 1
<211> LENGTH: 30
<212> TYPE: DNA
<213> ORGANISM: Artificial Sequence
<220> FEATURE:
<223> OTHER INFORMATION: Description of Artificial Sequence:synthetic
      DNA

<400> SEQUENCE: 1
gcggatccgt ggagttactc tcgttttttgc                                    30

<210> SEQ ID NO 2
<211> LENGTH: 49
<212> TYPE: DNA
<213> ORGANISM: Artificial Sequence
<220> FEATURE:
<223> OTHER INFORMATION: Description of Artificial Sequence:synthetic
      DNA

<400> SEQUENCE: 2
catagcagca ggatgaagag gaatatgata ggatgtgtct gcggcgttt              49

<210> SEQ ID NO 3
<211> LENGTH: 29
<212> TYPE: DNA
<213> ORGANISM: Artificial Sequence
<220> FEATURE:
<223> OTHER INFORMATION: Description of Artificial Sequence:synthetic
      DNA

<400> SEQUENCE: 3
gcaagctttc taacaacagt agtttccgg                                     29

<210> SEQ ID NO 4
<211> LENGTH: 50
<212> TYPE: DNA
<213> ORGANISM: Artificial Sequence
```

-continued

```
<220> FEATURE:
<223> OTHER INFORMATION: Description of Artificial Sequence:synthetic
      DNA

<400> SEQUENCE: 4
tcctctaatt ccaggatcaa caacaaccag aggttttgca tggtcccgta              50
```